(12) United States Patent
Zimmerman et al.

(10) Patent No.: US 6,297,277 B1
(45) Date of Patent: Oct. 2, 2001

(54) CYSTEINE PROTEASE INHIBITORS CONTAINING HETEROCYCLIC LEAVING GROUPS

(75) Inventors: Mary P. Zimmerman, Pleasonton; Robert E. Smith, Livermore, both of CA (US)

(73) Assignee: Prototek, Inc., Dublin, CA (US)

( * ) Notice: Subject to any disclaimer, the term of this patent is extended or adjusted under 35 U.S.C. 154(b) by 0 days.

(21) Appl. No.: 09/357,253

(22) Filed: Jul. 20, 1999

Related U.S. Application Data

(62) Division of application No. 08/921,683, filed on Sep. 2, 1997, now Pat. No. 5,925,772, which is a division of application No. 08/599,459, filed on Jan. 22, 1996, now Pat. No. 5,663,380, which is a division of application No. 08/164,031, filed on Dec. 8, 1993, now Pat. No. 5,486,623.

(51) Int. Cl.$^7$ ..................................................... A01N 37/12
(52) U.S. Cl. ................................................................ 514/534
(58) Field of Search ................................... 546/290, 300; 514/345, 351

(56) References Cited

U.S. PATENT DOCUMENTS

| | | | |
|---|---|---|---|
| 4,242,329 | 12/1980 | Claeson et al. | 424/177 |
| 4,518,528 | * 5/1985 | Rasnick et al. | 260/112.5 R |
| 4,835,253 | 5/1989 | Burton | 530/330 |
| 4,959,503 | * 9/1990 | Connor et al. | 564/265 |
| 5,158,936 | 10/1992 | Krantz et al. | 514/19 |
| 5,462,939 | 10/1995 | Dolle et al. | 514/231.5 |
| 5,486,623 | * 1/1996 | Zimmerman et al. | 549/417 |
| 5,663,380 | * 9/1997 | Zimmerman et al. | 549/475 |
| 5,925,772 | * 7/1999 | Zimmaerman et al. | 548/534 |
| 5,945,379 | * 8/1999 | Dollinger et al. | 504/130 |

FOREIGN PATENT DOCUMENTS

| | | |
|---|---|---|
| 0 056 015 A1 | 7/1982 | (EP). |
| 0 363 284 B1 | 4/1990 | (EP). |
| 0 525 420 A1 | 2/1993 | (EP). |
| 0 618 223 A2 | 10/1994 | (EP). |
| 1-163162 | 6/1989 | (JP). |
| WO 92/04371 | 3/1992 | (WO). |

OTHER PUBLICATIONS

Smith, R.A., et al., J. Am. Chem. Soc. (1988), 110, pp. 4429–4431.

Teno, N. et al., Chem. Pharm. Bull. 41(6) 1079–1090 (1993), Development of Active Center–Directed Plasmin and Plasma Kallikrein Inhibitors and Studies on the Structure--Inhibitory Active Relationship.

Simon, M. et al., Journal of Cellular Biochemistry 40:1–13 (1989), An Inhibitor Specific for the Mouse T–Cell Associated Serine Proteinase 1 (TSP–1) Inhibits the Cytolytic Potential of Cytoplasmic Granules but Not of Intact Cytolytic T Cells.

Simon M. et al., Chemical Abstracts, vol. 111, No. 76331q, (1989) An Inhibitor Specific for the Mouse T–Cell Associated Serine Proteinase 1 (TSP–1) Inhibits the Cytolytic Potential of Cytoplasmic Granules but Not of Intact Cytolytic T Cells.

* cited by examiner

Primary Examiner—Sabiha Qazi

(57) ABSTRACT

A class of cysteine protease inhibitors which inactivate a cysteine protease by covalently bonding to the protease and releasing a heterocyclic leaving group is presented. The cysteine protease inhibitors of the present invention comprise a first portion which targets a desired cysteine protease and positions the inhibitor near the thiolate anion portion of the active site of the protease, and a second portion which covalently bonds to the cysteine protease and irreversibly deactivates that protease by providing a carbonyl or carbonyl-equivalent which is attacked by the thiolate anion of the active site of the cysteine protease to sequentially cleave a heterocyclic leaving group. The heterocyclic leaving group of the protease inhibitor is of the formula: —O—Het, where Het is a heterocycle having 4–7 atoms in the ring, with at least one of the heterocycle atoms being N, O or S.

12 Claims, No Drawings

CYSTEINE PROTEASE INHIBITORS CONTAINING HETEROCYCLIC LEAVING GROUPS

This application is a divisional application of applicant's application Ser. No. 08/921,683, filed Sep. 2, 1997, now U.S. Pat. No. 5,925,772, which is a divisional application of Ser. No. 08/599,459, filed Jan. 22, 1996, now issued U.S. Pat. No. 5,663,380, which is a divisional of Ser. No. 08/164, 031, filed Dec. 8, 1993, now issued U.S. Pat. No. 5,486,623.

FIELD OF THE INVENTION

The present invention relates generally to cysteine protease inhibitors, and more particularly to cysteine protease inhibitors which are peptidyl ketones having heterocyclic leaving groups. The cysteine protease inhibitors of the present invention are particularly designed for the in vivo management of cysteine proteases, particularly cathepsins B, L, H and C, and their primitive enzymatic counterparts.

BACKGROUND TO THE INVENTION

Cysteine proteases associated with human disease states can be grouped into three categories: (1) lysosomal cathepsins; (2) cytosolic calpains; and (3) procaryotic enzymes with autocatalytic activation. Cathepsins B, H, and L are cysteinyl proteases involved in normal protein degradation. As such, they are generally located in the lysosomes of cells. When these enzymes are found extralysosomaly they have been implicated by use of synthetic substrate technology and by natural endogenous inhibitors as playing a causative rote in a number of disease states such as rheumatoid arthritis, osteo arthritis, *Pneumocystis carinii, Schistosomiasis, Trypanosoma cruzi, Trypanosoma brucei brucei, Crithidia fusiculata,* malaria, periodontal disease, tumor metastasis, metachromatic leukodystrophy, muscular dystrophy, etc. For example, a connection between cathepsin B-type enzymes and rheumatoid arthritis has been suggested in van Noorden and Everts, "Selective Inhibition of Cysteine Proteinases by Z-Phe-Ala-CH$_2$F Suppresses Digestion of Collagen by Fibroblasts and Osteoclasts," 178 *Biochemical and Biophysical Research Communications* 178; Rifkin, Vernillo, Kleekner, Auszmann, Rosenberg and Zimmerman, "Cathepsin B and L Activities in Isolated Osteoclasts," 179 *Biochemical and Biophysical Research Communications* 63; Grinde, "The Thiol Proteinase Inhibitors, Z-Phe-Phe-CHN$_2$ and Z-Phe-Ala-CHN$_2$, Inhibit Lysosomal Protein Degradation in Isolated Rat Hepatocytes," 757 *Biochimica et Biothysica Acta* 15; Mason, Bartholomew and Hardwick, "The Use of Benzyloxycarbonyl[$^{125}$I] iodotyrosylalanyldiazomethane as a Probe for Active Cysteine Proteinases in Human Tissues," 263 *Biochem. J.* 945; van Noorden, Smith and Pasnick, "Cysteine Proteinase Activity in Arthritic Rat Knee Joints and tile Effects of a Selective Systemic Inhibitor, Z-Phe-Ala-CH$_2$F," 15 *J. Rheumatol.* 1525; and van Noorden, Vogels and Smith, "Localization and Cytophotometric Analysis of Cathepsin B Activity in Unfixed and Undecalifed Cryostat Sections of Whole Rat Knee Joints," 37 *J. Histochemistry and Cytochemistry* 617. A connection between cathepsin B and osteo arthritis has been suggested in Delaisse, Eeckhout and Vaes, "In Vivo and In Vitro Evidence for the Involvement of Cysteine Proteinases in Bone Resorption," 125 *Biochemical and Biophysical Research Communications* 441; a connection between cathepsin B and pneumocystis carinii has been suggested in Hayes, Stubberfield, IcBride and Wilson, "Alterations in Cysteine Proteinase Content of Rat Lung Associated with Development of Pneumocystis Carinii Infection," 59 *Infection and Immunity* 3581; a connection between cysteine proteinases and schistosomiasis has been suggested in Cohen, Gregoret, Amiri, Aldape, Railey and McKerrow, "Arresting Tissue Invasion of a Parasite by Protease Inhibitors Chosen With the Aid of Computer Modeling," 30 *Biochemistry* 11221. A connection between cysteine proteinases and trypanosoma cruzi, trypanosoma brucei brucei and crithidia fasciculata has been suggested in Ashall, Harris, Roberts, Healy and Shaw, "Substrate Specificity and Inhibitor Sensitivity of a Trypanosomatid Alkaline Peptidase," 1035 *Biochimica et Biophysica Acta* 293, and/or in Ashall, Angliker and Shaw, "Lysis of Trypanosomes by Peptidyl Fluoromethyl Ketones," 170 *Biochomical and Biophysical Research Communications* 923. A connection between cysteine proteinases and malaria has been suggested in Rosenthal, Wollish, Palmer and Rasnick, "Antimalarial Effects of Peptide Inhibitors or a Plasmodium Falciparum Cysteine Proteinase," 88 *J. Clin. Invest* 1467, and in Rosenthal, Lee and Smith, "Inhibition of a Plasmodium Vinckei Cysteine Proteinase Cures lurine Mialaria," (in press). A connection between cathepsin B and tumor metathesis has been suggested in Smith, Rasnick, Burdick, Cho, Rose and Vahratian, "Visualization of Time-Dependent Inactivation of Human Tumor Cathepsin B Isozymes by a Peptidyl Fluoromethyl Ketone Using a Fluorescent Print Technique," 8 *Anti-cancer Research* 525. A connection between cathepsin B and cancer has been suggested in Gordon and Mourad, 2 *Blood Coaculation and Fibrinolysis* 735. A connection between cathepsin B and periodontal disease has been suggested in Cox, Cho, Eley and Smith, "A Simple, Combined Fluorogenic and Chromogenic Method for the Assay of Proteases in Gingival Crevicular Fluid," 25 *J. Periodont. Res.* 164; Uitto, Larjava, Helno and Sorsa, "A Protease of Bacteroides Gingivalis Degrades Cell Surface and M,latrix Glycoproteins of Cultured Gingival Fibroblasts and induces Secretion of Collagenase and Plasminogen Activator," 57 *Infection and Immunitv* 213; Kunimatsu, Yamamoto, Ichimaru, Kato and Kato, "Cathepsins B, H and L Activities in Gingival Crevicular Fluid From Chronic Adult Periodontitis Patients and Experimental Gingivitis Subjects," 25 *J Periodont Res* 69; Beighton, Radford and Naylor, "Protease Activity in Gingival Crevicular Fluid From Discrete Periodontal Sites in Humans With Periodontitis or Gingivitis"; 35 *Archs oral Biol.* 329; Cox and Eley., "Preliminary Studies on Cysteine and Serine Proteinase Activities in Inflamed Human Gingiva Using Different 7-Amino-4-Trifluoromethyl Coumarin Substrates and Protease Inhibitors," 32 *Archs oral Biol.* 599; and Eisenhauer, Hutchinson, Javed and McDonald, "Identification of a Cathepsin B-Like Protease in the Crevicular Fluid of Gingivitis Patients," 62 *J Dent Res* 917. A connection between cathepsin B and metachromatic leukodystrophy has been suggested in von Figura, Steckel, Conary, Hasilik and Shaw, "Heterogeneity in Late-Onset Metachromatic Leukodystrophy. Effect of Inhibitors of Cysteine Proteinases," 39 *Am j Hum Genet.* 371; a connection between cathepsin B and muscular leukodystrophy has been suggested in Valentine, Winand, Pradhan, Moise, de Lahunta, Kornegay and Cooper, "Canine X-Linked Muscular Dystrophy as an Animal Model of Duchenne Muscular Dystrophy: A Review," 42 *Am J Hum Genet* 352; a connection between cathepsin B and rhinovirus has been suggested in Knott, Orr, Montgomery, Sullivan and Weston, "The Expression and Purification of Human Rhinovirus Protease 3C," 182 *Eur. J. Biochem.* 547; a connection between cathepsin B and kidney disease has been suggested in Baricos, O'Connor, Cortez, Wu and Shah, "The Cysteine Proteinase Inhibitor, E-64, Reduces Proteinuria in an Experimental Model of Clomeruloneohritis," 155 *Biochemical and Biophysical Research Communications* 1318; and a connection between cathepsin B and multiple sclerosis has been suggested in Dahlman, Rutschmann, Kuehn and Reinauer, "Activation of the Multicatalytic Proreinase from Pat Skeletal Muscle by Fatty Acids or Sodium Dodecyl Sulphate," 228 *Biochem. J.* 171.

Connections between certain disease states and cathepsins H and C have also been established. For example, cathepsin H has been directly linked to the causative agents of Pneumocystis carinii and in the neuromuscular diseases Duchenne dystrophy, polymyositis, and neurogenic disorders. Stauber, Riggs and Schochet, "Fluorescent Protease Histochemistry in Neuromuscular Disease," Neurolooy 194 (Suppl. 1) March 1984; Stauber, Schochet, Riggs, Gutmann and Crosby, "Nemaline Rod Myopathy: Evidence for a Protease Deficiency," *Neurology* 34 (Suppl. 1) March 1984. Similarly, cathepsin C has been directly linked to muscular diseases such as nemaline myopathy, to viral infections, and to processing and activation of bone marrow serine proteases (elastase and granzyme A). McGuire, Lipsky and Thiele, "Generation of Active ivyeloid and Lymphod Granule Serine Proteases Requires Processing by the Granule Thiol Protease Dipeptidyl Peptidase I, 268 *J. Biol. Cohm.* 2458–67; L. Polgar, Mechanisms of Protease Action (1989); Brown, McGuire and Thiele, "Dipeptidyl Peptidase I is Enriched in Granules of in Vitro- and In Vivo-Activated Cytotoxic T Lymphocytes," 150 *Immunology* 4733–42. The Brown et al. study effectively demonstrated the feasibility of inhibiting cathepsin C (DPP-I) in the presence of other cysteinyl enzymes cased on substrate specificity. Unfortunately, the diazoketones used in that study are believed to be mutagenic and not appropriate for in vivo application.

The cytosolic or membrane-bound cysteine proteases called calpains have also been implicated in a number of disease states. For example, calpain inhibitor can be useful for the treatment of muscular disease such as muscular dystrophy, amyotrophy or the like, 25 Taisha (Metabolism) 183 (1988); 10 J. Pharm. Dynamics 678 (1987); for the treatment of ischemic diseases such as cardiac infarction, stroke and the like, 312 New Eng. J. Pled. 159 (1985); 43 Salshin Igaku 783 (1988); 36 Arzneimittel Forschung/Drug Research 190, 671 (1986); 526 Brain Research 177 (1990); for improving the consciousness disturbance or motor disturbance caused by brain trauma, 16 Nieurochemical Research 483 (1991); 65 J. Neurosurgery 92 (1986); for the treatment of diseases caused by the demyelination of neurocytes such as multiple sclerosis, peripheral nervous neuropathy and the like, 47 J. Neuochemistry 1007 (1986); and for the treatment of cataracts, 28 Investigative Ophthalmology & Visual Science 1702 (1987); 34 Experimental Eye Research 413 (1982); 6 Lens and Eye Toxicity Research 725 (1989): 32 Investigative Ophthalmology & Visual Science 533 (1991).

Calpain inhibitors may also be used as therapeutic agents for fulminant hepatitis, as inhibitors against aggregation of platelet caused by thrombin, 57 Thrombosis Research 847 (1990); and as a therapeutic agent for diseases such as breast carcinoma, prostatic carcinoma or prostatomegaly, which are suspected of being caused by an abnormal activation of the sex hormone receptors.

Certain protease inhibitors have also been associated with Alzheimer's disease. See, e.a., 11 Scientific American 40 (1991). Further, thiol protease inhibitors are believed to be useful as anti-inflammatory drugs, 263 J. Biological Chem. 1915 (1988); 98 J. Biochem. 87 (1985); as antiallergic drugs, 42 J. Antibiotics 1362 (1989); and to prevent the metastasis of cancer, 57 Seikagaku 1202 (1985); Tumor Progression and Markers 47 (1982); and 256 J. Biological Chemistry 8536 (1984)

Further, cysteine protease has been shown to process the convertase enzyme of interleukin-1, a cytokine that is implicated in septic shock, wound healing, and the growth of certain leukemia See, e.c., Thornberry et al., 356 Nature 755; Goll et al., 74 Biochimi 225 (1992), and Bioworld Today, Vol. 3, No. 67, p. 1, Apr. 3, 1992.

Although a number of cysteine proteinase inhibitors have been identified, most of these have drawbacks for in vivo use. In particular, drawbacks such as reversibility of inhibition, lack of specificity, and rapid clearance from, the body have been associated with prior art inhibitors. The microbial products antipain and leupeotin, for example, are effective but reversible inhibitors of cysteine proteinase (McConnell et al., 33 *J. Med. Chem.* 86–93; Sutherland et al. 110 *Biochem. Biophys. Res. Commun.* 332–38), and also inhibit certain serine proteinases (Umezawa, 45 *Meth. Enzymol.* 678–95). The compound E64 and its synthetic analogues are more selective inhibitors (see, e.g., Barret et al., 201 *Biochem. J.* 189–98, and Grinde, 701 *Biochem. Biophys. Acta.* 328–33), but disappear too quickly from the circulation for in vivo use (Hashida et al. 91 *J. Biochem.* 1373–80).

To date, two classes of peptidyl ketone inhibitors have been identified. One class, originally described by Abeles, comprises reverible inhibitors of both serine and cysteine proteases. For example, Abeles et al. describe trifluoromethyl ketones of the form:

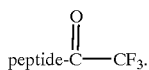

Abeles et al., "Fluoroketone Inhibitors of Hydrolytic Enzymes," 24 *Biochemistry* 1813–17, (1985).

Similarly, reversible inhibitors to serine proteases also exist in their hydrated form:

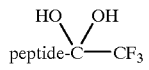

and therefore become transition state analog inhibitors. Further, Hu et al., "Inhibition of Cathepsin B and Papain by Peptidyl α-ketoEsters, α-ketoAmides, α-Diketones, and α-ketoAcids", 281 *Archives of Biochemistry and Biophysics* 271–274 (1990) describe compounds of similar reactivity of the form:

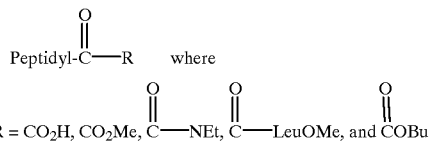

Most recently, European Patent publication EPO-525420-A1 disclosed peptidyl ketones that were activated by the permanent (nonfissionable) placement of methylthiomethyl ring or amine, thus making reversible inhibitors of reduced efficacy.

The difference between these noncleavable reversible inhibitors and the irreversible inhibitors of the present invention is that the former inhibitors remain intact in the active site constantly partitioning with the external medium while the latter cleaves and leaves the peptide portion irreversibly bonded to the enzymes active site, thereby permanently disabling the enzyme. This latter mechanism translates into lower required doses of therapeutic agent.

The most promising type of cysteine proteinase inhibitors have an activated carbonyl with a suitable α-leaving group fused to a programmed peptide sequence that specifically directs the inhibitor to the active site of the targeted enzyme. Once inside the active site, the inhibitor carbonyl is attacked by a cysteine thiolate anion to give the resulting hemiacetal, which collapses via a 1,2-thermal migration of the thiolate and subsequent displacement of the α-keto-leaving group. The bond between enzyme and inhibitor is then permanent and the enzyme is irreversibly inactivated.

The usefulness of an inhibitor in inactivating a particular enzyme therefore depends not only on the "lock and key" fit of the peptide portion, but also on the reactivity of the bond holding the α-leaving group to the rest of the inhibitor. It is important that the leaving group be reactive only to the intramolecular displacement via a 1,2-migration of sulfur in the breakdown of the hemithioacetal intermediate.

Groundbreaking Work regarding cysteine oroteinase inhibitors having an activated carbonyl, a suitable α-leaving group and a peptide sequence that effectively and specifically directs the inhibitor to the active site of the targeted enzyme was disclosed in U.S. Pat. No. 4,518,528 to Rasnick, incorporated herein by reference. That patent established peptidyl fluoromethyl ketones to be unprecedented inhibitors of cysteine proteinase in selectivity and effectiveness The fluoromethyl ketones described and synthesized by Rasnick included those or the formula:

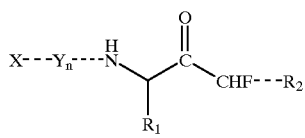

wherein $R_1$ and $R_2$ are independently selected from the group hydrogen, alkyl of 1–6 carbons, substituted alkyl of 1–6 carbons, aryl, and alkylaryl where the alkyl group is of 1–4 carbons; n is an integer from 1–4 inclusive; X is a peptide end-blocking group; and Y is an amino acid or peptide chain of from 1–6 amino acids.

Peptidylketone inhibitors using a phenol leaving group are similar to the peptidyl fluoroketones. As is known in the art, oxygen most closely approaches fluorine in size and electronegativity. Further, when oxygen is bonded to an aromatic ring these values of electronegativity become even closer due to the electron withdrawing effect of the $sp^2$ carbons. The inductive effect of an α-ketophenol versus an α-ketofluoride when measured by the pKa of the α-hydrogen, appears comparable within exoerimerntal error.

Unfortunately, the leaving groups of prior art cysteine protease inhibitors have presented problems of toxicity, solubility, etc. For example, the inhibitors disclosed by Krantz et al. in U.S. Pat. No. 5,055,451 have been found to be unacceptably toxic when introduced into animals such as rabbits or dogs.

A need therefore exists for cysteine protease inhibitors with improved solubility and toxicity profiles, and which are particularly suitable for in vivo use. The present invention addresses that need.

SUMMARY OF THE INVENTION

Briefly describing the present invention, there is provided a class of cysteine protease inhibitors which deactivates the protease by covalently bonding to the cysteine protease and releasing a heterocyclic leaving group. The cysteine protease inhibitors of the present invention accordingly comprise a first portion which targets a desired cysteine protease and positions the inhibitor near the thiolate anion portion of the active site of the protease, and a second portion Which covalently bonds to the cysteine protease and irreversibly deactivates that protease by providing a carbonyl or carbonyl-equivalent which is attacked by the thiolate anion or the active site of the cysteine protease to sequentially cleave a heterocyclic leaving group. The heterocyclic leaving group of the protease inhibitor is of the formula: —O—Het, where Het is a heterocycle having 1–7 members in the ring, with at least one of the heterocycle members being N, O or S.

One object of the present invention is to provide improved cysteine protease inhibitors with improved solubility and toxicity profiles.

A further object of the present invention is to provide a class of cysteine protease inhibitors which are particularly effective for in vivo applications.

Further objects and advantages of the present invention will be apparent from the following description.

DESCRIPTION OF THE PREFERRED EMBODIMENT

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

As indicated above, the present invention relates to cysteine protease inhibitors which contain heterocyclic leaving groups. In one aspect of the invention, a group of cysteine protease inhibitors which have been shown to be particularly effective for in vivo applications is disclosed.

The cysteine protease inhibitors described herein function as the sum of two portions. The first portion defines the specificity of a particular inhibitor to an enzyme by the spacial, hydrophobic or hydrophilic and ionic interactions of a particular composition that either imitates or improves upon the nature of the enzyme's natural substrate. The second portion is a trap that covalently binds the enzyme in a two-step mechanism: the first step involves the nucleophilic attack of the enzyme thiolate on the carbonyl of the inhibitor to form a hemithioketal. It is then energetically favorable for this intermediate to undergo a 1,2 migration of the thiolate in which a heterocyclic leaving group is simultaneously released. The enzyme has now become irreversibly bonded to the inhibitor. With the inhibitors of the present invention the leaving group is a heterocyclic leaving group.

Accordingly, the cysteine proteinase inhibitors of the present invention are preferably constructed with an activated carbonyl which bears a suitable α-leaving group which is fused to a programmed peptide sequence that specifically directs the inhibitor to the active site of the targeted enzyme. (For example, Z-Phe-PheCHN$_2$ preferentially inhibits cathepsin L over catheosin B.) Once inside the active site, this inhibitor carbonyl is attacked by a cysteine thiolate anion to give the resulting hemiacetal form. If the α-leaving group then breaks off, the bond between enzyme and inhibitor becomes permanent and the enzyme is irreversibly inactivated. The selectivity of the inhibitor for a particular enzyme depends not only on the "lock and key" fit of the peptide portion, but also on the reactivity of the bond binding the leaving group to the rest of the inhibitor. It is very important that the leaving group must be reactive only to the intramolecular displacement via a 1,2-migration of sulfur in the breakdown of the hemithioacetal intermediate.

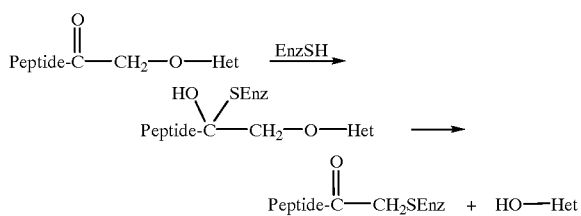

The preferred inhibitors of the present invention can be described generally by the formula:

wherein B is an amino acid blocking group for the N-terminal amino acid, each $(P)_x$ is an optionally protected α-amino acid residue, x is an integer between zero and 5, inclusive, and Het is the heterocyclic portion of the leaving group.

As is conventional in the art, and as used herein, amino acid residues may be designated as $P_1$, $P_2$, etc., wherein $P_1$ refers to the amino acid residue nearest the leaving group, $P_2$ refers to the amino acid residue next to $P_1$ and nearer the blocking group, etc. In dipeptide inhibitors therefore, $P_2$ is the amino acid residue nearest the blocking group.

More specifically, the compounds employed in the present invention are of the formula:

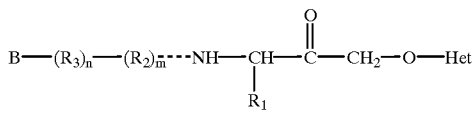

wherein
B is H or an amino acid blocking group for an N-terminal amino acid nitrogen;
$R_1$ is the amino acid side chain of the $P_1$ amino acid residue;
$R_2$ is the amino acid residue of the $P_2$ amino acid;
$R_3$ is the amino acid residue of the $P_3$ amino acid;
n is 0 or 1;
m is 0 or 1; and
Het is the heterocyclic portion of the leaving group; wherein the heterocyclic leaving group includes a four-, five-, six- or seven-membered ring having at least one C and at least one of N, O or S in the ring.

Concerning the amino acid blocking group B for the N-terminal amino acid nitrogen, many suitable peptide end-blocking groups are known in the art. For example the end-blocking groups identified in E. Gross and J. Meienhofer (eds.), *The Peptides*, Vol. 3 are generally suitable for use in the present invention. Preferred blocking groups include N-morpholine carbonyl and derivatives of propionic acid derivatives that have intrinsic analgesic or anti-inflammatory action. Examples of blocking groups having intrinsic analgesic or anti-inflammatory action may be found in Gilman, Goodman, Gilman, *The Pharmacological Basis of Therapeutics*, Sixth Ed. MacMillan, Chapter 29. As defined herein, the peptide end-blocking group is attached to either an amino acid or a peptide chain.

One particularly effective blocking group is the 4-morpholinylcarbonyl ("Mu") blocking group shown below:

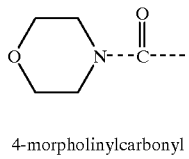

4-morpholinylcarbonyl

The peptide portion of the inhibitor may include any pep,ide appropriate for targetting a desired cysteine protease. Preferably, the side chain on the $P_1$ amino acid is selected according to the enzyme being targetted. For cathepsin B or L, this might include side chains such that the linked $P_1$ amino acid is a member of the group consisting of alanyl (Ala), arginyl (Arg), aspartic acid (Asp), glutamic acid (Glu), histidyl (His), homophenylalanyl (HPhe), phenylalanyl (Phe), ornithyl (Orn), seryl (Ser) and threonyl (Thr), and optionally substituted analogues thereof such as thiazoles and amino thiazoles. Preferably the side chain on the P amino acid is selected so that the linked $P_2$ amino acid is a member of the group consisting of phenylalanyl (Phe), leucyl (Leu), tyrosyl (Tyr) and valyl (Val) amino acid residues and substituted analogues thereof, particularly including Tyr(OMe).

As indicated above, each of the cysteine protease inhibitors of the present invention includes a heterocyclic leaving group. The heterocycle of the leaving group is a ring of variable size (4–7 members) containing one or more heteroatoms and n double bonds where n=0–3. This ring is bonded through an oxygen atom which becomes part of the leaving group during inhibition of the targeted enzyme. In the absence of the targeted active site, the inhibitor construction is an ether that is very stable in the physiological environments of the stomach, lysosome, or disease state arthritic joint.

The heterocycles of the present invention may be derived from the group that includes pyridine n-oxides, uracils, cytosines, pyrones, pyridones, pyrimidines, pyraziznes, furans, thiophenes, pyrroles, oxazoles, thiazoles, pyrazoles, imidazoles, triazoles, tetrazoles and their optionally-substituted derivatives such as benzo-fused derivatives. For oral bioavailability, the most preferred leaving groups have at least one heteroatom for each four carbon atoms in the leaving group.

The ability of the leaving group to protonate at physiological pH is directly related to its inability to cross cell membranes Which can be advantageous in certain applications. In the same context, the ability of a heterocycle to chelate with a metal ion may (1) impede crossing of membranes and/or (2) target metalloproteases such as calpains. In the environment of the active site protonation and/or hydrogen bonding of ring heteroatoms will accentuate its role as a leaving group.

It is to be appreciated that the heterocycle may be chosen specifically in accord With the function of the enzyme to be inhibited. For example, the inhibitor would use a derivative of hydroxyproline (a major constituent of collagen) to target a collagenase:

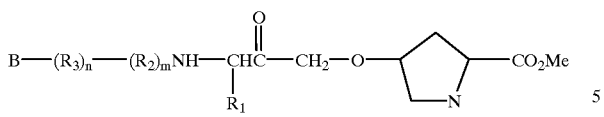

or the natural substrate (hydroxyproline) may be improved upon by a suitable replacement such as a hydroxyfuran which upon displacement from the inhibitor can and does tautomerize to a more stable keto form increasing its efficiency as a leaving group.

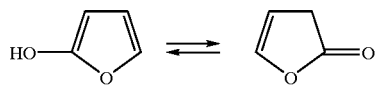

It is also to be aporeciated that during the course of the reaction of enzyme with inhibitor, the carbonyl of the inhibitor rehybridizes to sp3 and forms a ketal intermediate with the thiol function of the enzyme. Under the acid conditions of this reaction, other ketals can exchange with this intermediate either by going through the ketone or by ketal-ketal exchange. Accordingly, ketals can be substituted for carbonyls in the peptidyl inhibitors of the present invention. Similarly, other compounds such as hydrazones, hemiketals, oximes, imines, cyanohydrins, enolethers, enamines, hemithioketals, and the like are to be considered carbonyl equivalents and may be substituted for a carbonyl or to give a carbonyl under the acidic conditions of these inhibition reactions. Utilization of such derivatives can also be vehicles to either improve the bioavailability of the inhibitor drug or keep it from crossing a cellular membrane depending upon the hydrophobic nature of the masking function.

Finally, it is to be appreciated that the development and synthesis of compounds having isosteric replacements of amide bonds is now a standard practice in the development of biologically active peptides once the optimum peptide sequence has been identified. Accordingly, the present invention includes compounds having one or more modified amide bonds in the peptide sequence so long as conformation and binding are maintained while secondary enzymatic hydrolysis is prevented.

For a list of such modifications see Kaltenbronn, 33, *J. Med. Chem.*, 838. In addition, inhibitors having a hydrazine replacement for the $P_1$ nitrogen as reported by Giordano for other halogen methyl ketones are also intended to be claimed.

Reference will now be made to specific examples using the processes described above. It is to be understood that the examples are provided to more completely describe preferred embodiments, and that no limitation to the scope of the invention is intended thereby.

EXAMPLE 1

Synthesis of

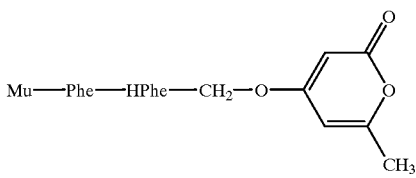

In a 100 ml round bottom flask equipped with an argon line was placed Mu-Phe-H[]he-Br (1.0 g, 1.94 mmol), potassium fluoride (449.5 mg, 7.75 mmol), potassium carbonate (534.9 mg, 3.87 mmol)-$K_2CO_3$ was added to control the acidic environment, and 4-hydroxy-6-methyl-2-pyrone (488.0 mg, 3.87 mmol). About 5 ml of DMF was added to dissolve the solid mixture. The reaction flask was immersed in a 50° C. oil bath. The reaction was allowed to run for 40 minutes in order to ensure the completion of the reaction. The reaction mixture Was diluted with ethyl acetate, and potassium fluoride was removed by a small silican gel column. The solvent ethyl acetate was stripped by a water vacuum pump, and DMF was removed by an oil vacuum pump. The next day the light yellow product was recrystallized in hexane:diethyl ether (50%:50%). The white precipitate was filtered and a NMP spectrum was obtained. m.p. 94–98° C.

EXAMPLE 2

Synthesis of

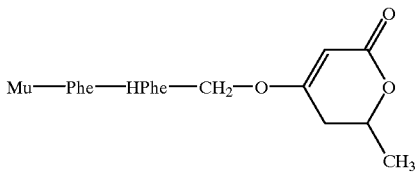

In a 100 ml round bottom flask equipped with an argon line as placed Mu-Phe-HPhe-Br (300 mg, 0.581 mmol), potassium fluoride (134.8 mg, 2.33 mmol) potassium carbonate (321.4 mg, 2.33 mmol)-$K_2CO_3$ was added to control the acidic environment, and 5,6-dihydro-4-hydroxy-6-methyl-2H-pyran-2-one (298.0 mg, 2.33 mmol). About 5 ml of DMF was added to dissolve the solid mixture. The reaction flask was immersed in a 50° C. oil bath. The reaction was allowed to run for 40 minutes in order to ensure the completion of the reaction. The reaction mixture was diluted with ethyl acetate, and potassium fluoride was removed by a small silica gel column. The solvent ethyl acetate was removed by a water vacuum pump, and DMF was removed by an oil vacuum pump. The next day the light yellow product was recrystallized in 50:50 hexane:diethyl ether. The white precipitate was filtered and a NMR spectrum was obtained. m.p. 74–7° C.

EXAMPLE 3

Synthesis of

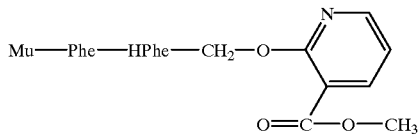

In a 100 ml round bottom flask equipped with an argon line was placed Mu-Phe-HPhe-Br (1 g, 1.94 mmol), potassium fluoride (0.45 g, 7.75 mmol), potassium carbonate (1.07 g, 7.75 mmol)-$K_2CO_3$ was added to control the acidic environment, and 2-hydroxy-3-methylcarboxypyridine (0.59 g, 3.87 mmol). About 5 ml of DMF was added to dissolve the solid mixture. The reaction flask was immersed in a 50° C. oil bath. The reaction was allowed to run for 40 minutes in order to ensure the completion of the reaction. The reaction mixture was diluted with ethyl acetate, and potassium fluoride was removed by a small silica gel column. The solvent ethyl acetate was removed by a water vacuum pump, and DMF was removed by an oil vacuum pump. The next day the light yellow product was recrystallized in 50:50 hexane:diethyl ether. The white precipitate was filtered and a NMR spectrum was obtained. m.p. 100–102° C.

EXAMPLE 4

Synthesis of

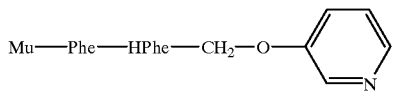

In a 100 ml round bottom flask equipped with an argon line was placed Mu-he-HPhe-Br (500 mg, 0.969 mmol), potassium fluoride (224.8 mg, 3.876 mmol), potassium carbonate (267.8mg, 1.938 mmol)-$K_2CO_3$ was added to control the acidic environment, and 3-hydroxypyridine (184.3 mg, 1.938 mmol). About 5 ml of DMF was added to dissolve the solid mixture. The reaction flask was immersed in a 50° C. oil bath. The reaction was allowed to run for 40 minutes in order to ensure the completion of the reaction. The reaction mixture was diluted with ethyl acetate, and potassium fluoride was removed by a small silica gel column. The solvent ethyl acetate was removed by a water vacuum pump, and DMF was removed by an oil vacuum pump. The next day the light yellow product was recrystallized in 50:50 hexane:diethyl ether. The white precipitate was filtered and a NMR spectrum was obtained. m.p. 112–115° C.

EXAMPLE 5

Synthesis of

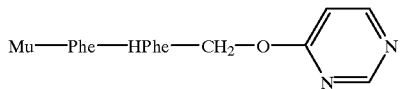

In a 100 ml round bottom flask equipped with an argon line was placed Mu-Phe-HPhe-Br (300 mg, 0.581 mmol), potassium fluoride (135.1 mg, 2.33 mmol), potassium carbonate (322.0 mg, 2.33 mmol)-K2Co3 was added to control the acidic environment, and 2-hydroxypyrimidine (111.7 mg, 1.938 mmol). About 5 ml of DMF was added to dissolve t-he solid mixture. The reaction flask was immersed in a 50° C. oil bath. The reaction was allowed to run for 40 minutes in order to ensure the completion of the reaction. The reaction mixture was diluted with ethyl acetate, and potassium fluoride was removed by a small silica gel column. The solvent ethyl acetate was removed by a water vacuum pump, and DMF was removed by an oil vacuum pump. The next day the light yellow product was recrystallized in 50:50 hexane:diethyl ether. The white precipitate was filtered and a NMR spectrum was obtained. m.p. 95–100° C.

EXAMPLE 6

Synthesis of

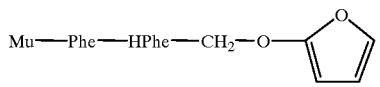

In a 100 ml round bottom flask equipped with an argon line was placed Mu-Phe-HPhe-CH -Br (500 mg, 0.969 mmol), potassium 2fluoride (224.8 mg, 3.876 mmol), potassium carbonate (535.7 mg, 3.876 mmol)-$K_2CO_3$ was added to control the acidic environment, and 2-furanone (275 μl, 3.876 mmol). About 5 ml of DMF was added to dissolve the solid mixture. The reaction flask was immersed in a 50° C. oil bath. The reaction was allowed to run for 40 minutes in order to ensure the completion of the reaction. The reaction mixture was diluted with ethyl acetate, and potassium fluoride was removed by a small silica gel column. The solvent ethyl acetate was removed by a water vacuum pump, and DMF was removed by an oil vacuum pump. The next day the light yellow product was recrystallized in 50:50 hexane:diethyl ether. The white precipitate was filtered and a NMR spectrum was obtained. m.p. 90–93° C.

EXAMPLE 7

Synthesis of

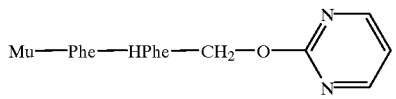

In a 100 ml round bottom flask equipped with an argon line was placed Mu-Phe-HPhe-Br (200 mg, 0.388 mmol), potassium fluoride (89.9 mg, 1.55 mmol), potassium carbonate (214.3 mg, 1.55 mmol)-$K_2CO_3$ was added to control the acidic environment, and 2-hydroxypyrimidine (205.5 mg, 1.55 mmol). .bout 4 ml of DMF was added to dissolve the solid mixture. The reaction flask was immersed in a 50° C. oil bath. The reaction was allowed to run for 40 minutes in order to ensure the completion of the reaction. The reaction mixture was diluted with ethyl acetate, and potassium fluoride was removed by a small silica gel column. The solvent ethyl acetate was removed by a water vacuum pump, and DMF was removed by an oil vacuum pump. The next day the light yellow product was recrystallized in 50:50 hexane:diethyl ether. The white precipitate was filtered and a NMR spectrum was obtained. m.p. 82–85° C.

EXAMPLES 8–9

Synthesis of

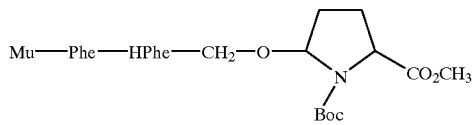

(MuPheHPhe-0-(proline methyl ester)).

In a 100 ml round bottom flask equipped with an argon line was placed Mu-Phe-HPhe-Br (500 mg, 0.969 mmol), potassium fluoride (224.8 mg, 3.876 mmol), potassium carbonate (535.7 mg, 3.876 mmol) was added to control the acidic environment, and Boc-L-hydroxyproline-methylester (475.2 mg, 1.938 mmol). About 6 ml of DMF was added to dissolve the solid mixture. The reaction was left at the room temperature and periodical TLC was checked to monitor the progress of the reaction. According to TLC, the reaction was completed after about one hour. The reaction mixture was diluted with ethyl acetate, and potassium fluoride was removed by a short silica gel column. The solvent ethyl acetate was stripped by a water vacuum pump, and DMF was removed by an oil vacuum pump. The product was dried under the vacuum pump. The next day the light yellow oily product was recrystallized in hexane. The precipitate was filtered and a NADIR spectrum was obtained.

De-Boc: About 5 ml of methylene chloride was used to dissolve 100 mg of the Boc product. Then about 5 ml of HCl. Dioxane was put into the 50 ml flask, and the reaction was allowed to proceed for about 45 minutes under argon. Carbon dioxide was released from the flask; bubbles came up to the surface of the reaction mixture. After the completion of the reaction, the mixture was slowly dropped into six test tubes filled with diethyl ether. The precipitation came out and was allowed to continue for about half hour. The product was quickly removed through suction filtration and it was put in a dry box overnight.

EXAMPLE 10

Synthesis of Mu-Phe-HPhe-CH$_2$-O-CH$_2$CH$_3$

In a 100 ml round bottom flask equipped with an argon line was placed Nu-Phe-HPhe-CH$_2$-Br (300 mg, 0.582 mmol), potassium fluoride (150 mg, 2.4 mmol), and potassium carbonate (150 mg, 1.2 mmol), and 8 ml of 200 proof ethanol. The reaction was stirred 3 hours, filtered and the solvents were removed under vacuum and the residue chromatographed on a short silica gel column (CHCl$_3$:MLEOH 95:5) and then recrystallized from ether.

EXAMPLE 11

General Procedure for the Preparation of HCl-HPhe-CH$_2$-O-Substituted Heterocyclic Inhibitors.

(a) BOC-HPhe Diazoketone

To BOC homophenylalanine (18 mmol) in 150 ml distilled THF at −20° C. was added one equivalent of N-methylmorpholine followed by one equivalent of isobutylchloroformate. After 10 minutes, the mixture was poured through filter paper into 200 ml etheral solution of diazomethane which was made according to the suppliers directions from 8.6 g of Diazald (Aldrich). The reaction was allowed to stir overnight, and then poured into 100 ml water. The organic portion was washed With NaHCO3(ag) (2×50 ml), brine (2×50 ml); dried over MgSO$_4$; concentrated to give the diazoketone 5.38 9 (99%) of a yellow oil that crystalizes on standing.

(b) BOC-HPhe-CH$_2$Br

To the above diazoketone (5.38 g, 0.018 mol) in 20 ml of methylene chloride at −5° C. is added dropwise 30% HBr in acetic acid which is diluted three-fold with methylene chloride. The addition is made at a rate that allows the monitoring of the evolved nitrogen and until all yellow color of the starting material has disappeared. The reaction is poured into 50 ml water and diluted with another 100 ml of methylene chloride. The organic layer is separated, washed with NaHCO$_3$ (aq) (50 ml), brine (50 ml), dried over MgSO and concentrated to give a white solid which is characterized by its NMIP.

(c) BOC-HPhe-CH$_2$-O-Substituted Heterocycle

In a 100 ml round bottom flask equipped with an argon line was placed BOC-HPhe-CH Br (1.4 mmol), potassium fluoride (5.5 mmol) and the substituted phenol (5.6 mmol). About 1 ml or DMF is added and the mixture is stirred at 50° C. for 40 min. The reaction is then diluted with ethyl acetate and run through a silica gel plug to remove the potassium salts. The solvents are removed (low then high) vacuum to give a solid product. When purification is needed, a silica gel column is used. In this way the following compounds were prepared:

| | Important NMR Signals (100 MHz, CDCl$_3$) | | |
|---|---|---|---|
| Compound | BOC | O<br>C-CH$_2$-O | O-Het-R |
| BOC-HPhe-O-Methyl nicotinate | 1.44 | 4.95 | 3.875 |
| BOC-HPhe-O-furan | 1.44 | 4.8 | |
| BOC-HPhe-O-methyl pyrone | 1.44 | 4.8 | 2.6 |

(d) Preo HCl—HPheCH$_2$2-O-Substituted heterocycle

To the BOC-PHhe CH$_2$-O-Substituted Aromatic (2.6 mmol) in 3 ml of methylene chloride was placed 8ml of 2N HCl—dioxane. The reaction was stirred about 40 min and the resulting mixture was added dropwise to about 600 ml of ether and then filtered to give the peptide inhibitor.

EXAMPLES 12–13

Evaluation of Heterocyclic-Methyl, Peptidyl Ethers by the in vitro Inhibition of Purified Enzymes Cathepsin B and H

EXAMPLE 12

Fluoroketone—Cathepsin B Kinietics

Enzyme: Cathepsin B, purified from human liver, is from Enzyme Systems Products (Dublin, Calif.). The activity is 50 mU per ml at 30° C., in 52 mM sodium phosphate, pH 6.2, 31 mM DTT, 2.1 mM EDTA, with 0.2 mM Z-Arg-Arg-7-amino-4-trifluoromethyl-coumarin as a substrate. Specific activity is 8330 mU per mg protein. (1 mU=1 nmol per min.)

Substrate: Boc-Leu-Arg-Arg-7-amino-4-triflouromethyl-coumarin-2HBr is from Enzyme Systems Products. A 20 mM solution is made in DMF and stored at −200 C.

Inhibitors: Candidate inhibitors are synthesized by Pcrototek, Inc., Dublin, Calif. 20 mM stock solutions are made in DMF and stored at −20° C. Dilutions are made in assay buffer.

Method: The percent inhibition and the inhibitor concentration at which the enzyme is 50% inhibited (IC50) are determined as follows:

Five µl of enzyme are activated by pre-incubation in three 480 µl aliquots and one 485 µl aliquot of assay buffer (50 mM potassium phosphate pH 6.2, 2 mM EDTA, 5 mM DTT) on ice for 30 min. The inhibition is initiated by the addition of 5 μL or 200 μM, 20 μM, and 2 μM inhibitor each to the 480 μl aliquots. The 485 μl aliquot zenith enzyme is used as a control and thus receives no inhiibitor. The enzyme/inhibitor mixtures are incubated 10 min. on ice and assayed for cathepsin B activity as follows.

Cathepsin B assay: To 490 μl of ore-incubated inhibitor/enzyme mixtures in assay buffer in 0.5 ml cuvette at 37° C. is added 10 μl or the s,ubstrate. Final inhibitor concentrations become 2000 mM, 200 mM, and 20 mM for the 200 μM, 20 μl and 2 μM stock concentrations, respectively. Activity is followed by release of free AFC over 5 min. (where (fluorescence units at t=6)—(fluorescence units at t=1)) with a Perkin-Elmer LS-5B spectrofluorometer (ex= 400 nm, em=505 nm).

The percent inhibition is determined by comparing the change in fluorescence units of the three sample concentrations of inhibited enzyme to the change in fluorescence units off the control enzyme. 100−(fl. units·of sample/f1. units of control×100) gives percent inhibition.

The IC50 is ascertained by plotting percent inhibition vs. inhibitor concentration on the log scale. The IC50 is the concentration of inhibitor (nM) at which the enzyme is inhibited by 50%.

| ACTIVITY AGAINST Cathepsin B (in vitro) | |
|---|---|
| Inhibitor (Example number) | rel. (in vitro) |
| MuPhe HPhe CH$_2$-O-(methyl)pyrone (1) | 112.2 nM |
| MuPhe HPhe CH$_2$-O-(methyl)dihydro pyrone (2) | 567.5 nM |
| MuPhe HPhe CH$_2$-O-(methyl)nicotinate (3) | 25,100.0 nM |
| MuPhe HPhe CH$_2$-O-(3)-pyridine (4) | 66.8 nM |
| MuPhe HPhe CH$_2$-O-(4)-Pyrimidine (5) | 7,100.0 nM |
| MuPhe HPhe CH$_2$-O-(2)-furan (6) | 23.7 nM |
| MuPhe HPhe CH$_2$-O-(2)-Pyrimidine (7) | 631.0 nM |
| MuPhe HPhe CH$_2$-O-proline methyl ester | |
| N-Boc (8) | 42.2 nM |
| N-HCl (9) | 223.9 nN |

EXAMPLE 13
Fluoroketone—Cathepsin H Kinetics

The materials and methods were as disclosed above for Example 12—cathepsin B kinetics—except as follows:
 Enzyme: Cathepsin H
 Substrate: HBr-Arg-7-amino-4-trifluoromethyl-coumarin
 Methods: assay buffer is pH 6.8

| Activity Against Cathepsin H | |
|---|---|
| HCl.HPhe-O-(methyl)nicotinate | 10.0 nM |
| HCl.HPhe-O-(methyl)pyrone | 150.0 nM |

EXAMPLES 14–15
Testing Heterocycle and Phenolic Leaving Groups In Vivo.

Water solutions of inhibitor using either ethanol or DMSO as a cosolvent were made at 8000 nM, 800 nM and 160 nM concentrations with a minimum of solvent. Each rat was given a dose at time 0 and then individuals were sacrificed at 6 hrs, 12 hrs and 24 hrs. Doses were given either by injection or stomach tube.

The livers and kidneys were harvested and analyzed for Cathepsin B activity. In some individuals the urine was collected at 6, 12, 24 hrs and analyzed For the presence of inhibitor. The results for Examples 14 and 15 are shown in Tables 14 and 15 below.

TABLE 14

Inhibition of Cathepsin B (in vivo) of MuPheHPhCH$_2$—O—[methylpyrone]

| Animal | Hrs | Dose | Route | % Inh. | % Inhb Paired Animal | Mean % Inhb |
|---|---|---|---|---|---|---|
| 1 | 24 | contr. | inject. | | | |
| 2 | 24 | contr. | st | | | |
| 3 | 6 | 8000 | inject. | 99.6 | | 99.6 |
| 4 | 6 | 800 | inject. | 59.0 | 43.60 | 51.3 |
| 5 | 6 | 160 | inject. | 10.3 | 31.80 | 21.0 |
| 6 | 6 | 8000 | st. | 89.2 | | 90.4 |
| 7 | 6 | 800 | st. | 25.2 | | 25.7 |
| 8 | 6 | 160 | st. | 23.9 | 94.50 | 59.2 |
| 9 | 12 | 8000 | inject. | 89.3 | | 90.5 |
| 10 | 12 | 800 | inject. | 43.5 | 54.80 | 49.1 |
| 11 | 12 | 160 | inject. | 16.4 | 39.10 | 27.8 |
| 12 | 12 | 8000 | st. | 46.5 | 57.70 | 52.1 |
| 13 | 12 | 800 | st. | 9.6 | | 11.6 |
| 14 | 12 | 160 | st. | 15.9 | | 14.8 |
| 15 | 24 | 8000 | inject. | 94.9 | 64.70 | 79.8 |
| 16 | 24 | 800 | inject. | 40.9 | 57.40 | 49.2 |
| 17 | 24 | 160 | inject. | 35.9 | 23.30 | 29.6 |
| 18 | 24 | 8000 | st. | 66.8 | | 64.0 |
| 19 | 24 | 800 | st. | 22.8 | 97.50 | 60.2 |
| 20 | 24 | 160 | st. | 99.6 | | 99.2 |

The results shown in Table 14 demonstrate effective inhibition and long duration of action.

TABLE 15

Inhibition of Cathepsin B In Vivo using MuPheHPheCH$_2$O—[pyridine]

| Time (hrs) | Dose | Route | % Inhibition |
|---|---|---|---|
| 6 | 8,000 | injection | 63.9 |
| 6 | 800 | injection | 46.9 |
| 6 | 160 | injection | 35.6 |
| 12 | 8,000 | injection | 46.2 |
| 12 | 800 | injection | 32.7 |
| 12 | 160 | injection | 10.1 |
| 24 | 8,000 | injection | 62.7 |
| 24 | 800 | injection | 53.5 |
| 24 | 160 | injection | 42.6 |
| 6 | 8,000 | st. | 79.9 |
| 6 | 800 | st. | 54.1 |
| 6 | 160 | st. | 61.2 |
| 12 | 8,000 | st. | 83.7 |
| 12 | 800 | st. | 65.7 |
| 12 | 160 | st. | 61.6 |
| 24 | 8,000 | st. | 49.3 |
| 24 | 800 | st. | 49.2 |
| 24 | 160 | st. | 40.7 |

The results shown in Table 15 demonstrate effective inhibition with long duration of action.

EXAMPLE 16
Treatment of Rheumatoid Arthritis with Mu-Phe-HPhe-O-proline methyl ester DBA/Lac mice mere injected with 200 μg of type II chick collagen emulsified in Freund's complete adjuvant on day 0 and on day 21. Mu-Phe-HPhe-O-prolite methyl ester was suspended in an ethanol solution which was then diluted to 10% (aq) and administered by garage at a dose of 10 mg/kg/day to day 21 until sacrifice at day 49. The of joint inflammation was evaluated grossly at seven day intervals beginning on day 21.

The effect of oral administration of Nu-Phe-HPhe-O-proline methyl ester on the severity of bone lesions in adjuvant-induced arthritis was determined by evaluating osseous mineralization, periostat proliferation, bone erosion, joint space narrowing and osseous fragmentation. All lesions were scored on a scale of 0 (normal architecture) to 3 (severe or marked changes). Values calculated were mean values ±std. error of the mean. The "bone lesion severity" values of Mu-Phe-HPhe-O-proline methyl ester treated animals were significantly ($p<0.05$) lower than the values of control animals for each parameter tested.

The effect of oral administration of Mu-Phe-HPhe-O-proline methyl ester on the histological aspects of adjuvant-induced arthritis was determined by evaluating inflammation, focul ulcers, tibiotarsal joint cartilage destruction, bone destruction and periosteal proliferation. Inflammation was scored on a scale of 0 (no inflammation) to 3 (severe) based on the extent of edema and cell infiltration. Focul ulcer cartilage destruction was measured as the percent of articular cartilage surfaces with focal destruction which exposed underlying subchondral bone. Tibiotarsal joint cartilage destruction was measured as the percent of articulating surfaces with destruction of the subchondral bone. Values calculated were mean values 1 std. error of the mean. The "histological aspects" values of Mu-Phe-HPhe-O-proline methyl ester treated animals were significantly ($p<0.05$) lower than the values of control animals for each parameter tested.

EXAMPLE 17

Treatment of Rheumatoid Arthritis with Mu-Leu-HPhe-O-proline methyl ester.

DBA/Lac mice were injected with 200 μg of type II chick collagen emulsified in Complete Freund's Adjuvant on day 0 and on day 21. Mu-Phe-HPhe-O-proline methyl ester was suspended in phosohate buffered saline and administered by gavage from day 21 until sacrifice at day 35. Doses of between 3 mg/kg/day and 25 mg/kg/day were used, with the daily dosage being held constant over time for each test. The severity of joint inflammation was evaluated grossly as seven day intervals beginning on day 21.

The effect of oral administration of Mu-Phe-Hphe-O-proline methyl ester on the severity of bond lesions in adjuvant-induced arthritis was determined by evaluating osseous mineralization, periostat proliferation, bone erosion, joint space narrowing and osseous fragmentation. All lesions were scored on a scale of 0 (normal architecture) to 3 (severe oc marked changes) Values calculated were mean values ±1 std. error of the mean. The "bone lesion severity" values of Mu-Phe-HPhe-O-proline ethyl ester treated animals were significantly ($p<0.05$) lower than the values of control animals for each parameter tested.

EXAMPLE 18

Treatment of Rheumatoid Arthritis with Mu-Tyr(OMe)-HPhe-O-proline methyl ester.

Rats were injected with adjuvant on day 0 and were treated with Mu-Tyr-(OMe)-HPhe-O-proline methyl ester in ground diet from the time of adjuvant injection until sacrifice at day 32. Over the course of the disease, animals were evaluated in terms of a mean clinical score, a derived series of clinically observed parameters normalized to facilitate graphical presentation. lean paw volumes were also measured using !normalized units throughout the course of the disease. At the end of the study, the animal groups were sacrificed and evaluated by X-ray analysis.

The mean clinical scores of Mu-Tyr-(OMe)-HPhe-O-proline methyl ester treated rats were significantly lower than the scores for untreated animals. Similarly, mean paw volumes were also significantly reduced. The Example demonstrates the beneficial effect of Nu-Tyr-(OMe)-HPhe-O-proline methyl ester on adjuvant-induced arthritis.

EXAMPLE 19

Effectiveness of Heterocyclic Methyl Ketones on Human and Murine Malaria Paracytes.

| In Vitro Effectiveness of Heterocyclic Methyl Ketones (All assays with Z-Phe-Arg-AMC) | | |
|---|---|---|
| | IC50 VALUES | |
| | P. falciparum (Human malaria parasite) | P. vinckei (Mouse malaria parasite) |
| MuPheHPheCH$_2$—O—furan | 15 nM | 40 nM |
| MuPheHPHeCH$_2$—O—pyranone-CH$_3$ | 50 nM | 500 nM |
| MuPheHPHeCH$_2$—O—pyridine | 2 μM | 10 μM |

EXAMPLE 20

Treatment of Gingivitis with MU-Phe-HPhe-O-furan.

The effect of the inhibitor on gingival inflammation was studied by investigating its ability to prevent the development of experimental gingivitis. Twenty human subjects with healthy gingiva and no periodontal disease were recruited. The subjects received oral hygiene instruction and scaling prior to baseline. The test sites were the mesibuccal crevices on the upper first and second molars and premolars (bicuspids). Acrylic shields were made to cover the gingival margins of these teeth and were worn during oral hygiene to prevent brushing of the test and control sites. During the test period of three weeks the subjects were told to brush only the lower teeth and upper anteriors and to wear the shields during brushing. The left side was used as the test side and the right was the control side in 10 subjects. The sides were reversed in the other 10 subjects so the subjects could act as their own controls. Thirty second GCF samples were taken prior to clinical measurements at baseline and at 1, 2, 3 and 4 weeks. These were assayed for cathepsins B and L-like activities. Clinical measurements of gingival index (GI), gingival bleeding index (GBI) and plaque index (PLI) were taken at test and control sites at zero, one, two, three and four weeks. Following the baseline measurements the inhibitor and placebo were placed at test 2nd control sites and sealed in with Coe-pak for a week. The inhibitor and placebo were coded so that the study was blind. The GI, GBI and PLI and cysteine proteinase levels were compared at test and control sites. It was observed that the use of Mu-Phe-MPhe-O-furan reduced all parameters tested at the test sites. Mu-Phe-HPhe-O-furan can therefore be seen to be effective in treating periodontal diseases such as gingivitis.

In the following Examples 21–27, the active ingredient is the compound moroholine carbonyl-L-phenylalanyl-L-homophenyl alanyl methyl furanyl ether (see Example 6). However, other compounds of the present invention can be substituted thereof.

EXAMPLE 21

An injectable preparation buffered to a pH of 7 is prepared having the following composition

| Ingredients | |
| --- | --- |
| Active ingredient | 02 g |
| $KH_2PO_4$ buffer (0.4 M solution) | 2 ml |
| KOH (1N) | q.s. to pH 7 |
| Water (distilled, sterile) | q.s. to 20 ml |

EXAMPLE 22

An oral suspension is prepared having the following composition

| Ingredients | |
| --- | --- |
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE 23

| Ingredients | Quantity per tablet, mgs. |
| --- | --- |
| Active ingredient | 25 |
| cornstarch | 20 |
| lactose, spray dried | 153 |
| magnesium stearate | 2 |

EXAMPLE 24

| Ingredients | Quantity per tablet, mgs. |
| --- | --- |
| Active ingredient | 100 |
| lactose, spray dried | 148 |
| magnesium stearate | 2 |

EXAMPLE 25

| Ingredients | Quantity per tablet, mgs. |
| --- | --- |
| Active ingredient | 200 |
| cornstarch | 50 |
| lactose | 145 |
| magnesium stearate | 5 |

The above ingredients are mixed intimately and pressed into single scored tablets.

EXAMPLE 26

| Ingredients | Quantity per tablet, mgs. |
| --- | --- |
| Active ingredient | 108 |
| lactose | 15 |
| cornstarch | 25 |
| magnesium stearate | 2 |

The above ingredients are mixed and introduced into a hard-shell gelatine capsule.

EXAMPLE 27

| Ingredients | Quantity per tablet, mgs. |
| --- | --- |
| Active ingredient | 150 |
| lactose | 90 |

The above ingredients are mixed and introduced ;into a hard-shell gelatine capsule.

Topical Formulation

| Ingredients | Grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water q.s. | 100 |

All of the above ingredients, except water, are combined and heated to 60° C. with stirring. A sufficient quantity of water at 60° C. is then added with vigorous stirring to emulsify the ingredients, and water then added q.s. 100 g.

As previously indicated, the compositions of the present invention may be useful in treating disease states which are associated with cathepsins B, L, H or C. For example, the cathepsin C inhibitors of the present invention may be used to inhibit dipeptidyl peptidase I ("DPP-I") found in cytotoxic T lymphocytes, or to inhibit the processing enzyme of bone marrow serine proteases like elastase and granzyme A.

It is to be appreciated that vinylogous homologs of heterocycles (benzo-derivatives) would also be considered by those skilled in the art to be reactive in this context. For example, because a hydroxy pyridine derivative works as a leaving group, a hydroxyquinoline (5, 6, 7 or 8-hydroxy) would also work. Other examples of this principle of vinylogy in synthetic organic chemistry include:

(1) A Michael reaction is a vinylogous analog of an aldol condensation; and
(2) An $SN_2$ reaction is a vinylogous analog to an $SN_2$ reaction.

It is also to be appreciated that because sulfur falls below oxygen in the periodic table that S may replace O in the compositions and methods of the present invention and an effective cysteine protease inhibitor would result.

Finally, it is to be appreciated that the processing of viral proteins by virally encoded proteases plays a central role in the maturation of many viruses. Examples of viruses which have been associated With cysteine proteases are polio virus (3C proteases) encephalomycarditis virsu, rhinovirus and foot-and-mouth virus. Accordingly, the compositions of the present invention are believed to be useful therapeutic agents for the treatment of viral diseases.

While the invention has been illustrated and described in detail in the drawings and foregoing description, the same is to be considered as illustrative and not restrictive in character, it being understood that only the preferred embodiment has been shorn and described and that all changes and modifications that come within the spirit of the invention are desired to be protected.

What is claimed is:

1. Cathepsin inhibitors of the formula:

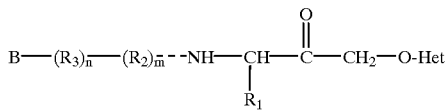

wherein

B is H or an amino acid blocking group for an N-terminal amino acid nitrogen;

$R_1$ is the amino acid side chain of the $P_1$ amino acid residue;

$R_2$ is the amino acid residue of the $P_2$ amino acid;

$R_3$ is the amino acid residue of the $P_3$ amino acid;

n is 0 or 1;

m is 0 or 1; and

Het is a pyridine or a substituted pyridine.

2. A cathepsin inhibitor according to claim 1 wherein n is 0 and m is 1.

3. A cathepsin inhibitor according to claim 2 wherein $R_2$ is the residue of phenylalanyl (Phe).

4. A cathepsin inhibitor according to claim 3 wherein $R_1$ is a side chain such that the $P_1$ amino acid residue is the residue of homophenylalanyl (HPhe).

5. A cathepsin inhibitor according to claim 4 wherein B is Mu.

6. A cathepsin dipeptidyl peptidase inhibitor according to claim 1 wherein B=H.

7. A cathepsin inhibitor according to claim 1 wherein Het is a benzo-fused pyridine.

8. A cathepsin inhibitor according to claim 1 wherein Het is a hydroxypyridine.

9. A cathespin H inhibitor according to claim 6 wherein Het is a pyridine.

10. A cathespin H inhibitor according to claim 7 wherein B=H, n=0 and m=0.

11. A cathepsin inhibitor according to claim 1, wherein said inhibitor is in a pharmaceutically acceptable carrier.

12. Cathepsin inhibitors of the formula:

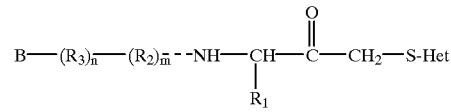

wherein

B is H or an amino acid blocking group for an N-terminal amino acid nitrogen;

$R_1$ is the amino acid side chain of the $P_1$ amino acid residue;

$R_2$ is the amino acid residue of the $P_2$ amino acid;

$R_3$ is the amino acid residue of the $P_3$ amino acid;

n is 0 or 1;

m is 0 or 1; and

Het is a pyridine or a substituted pyridine.

* * * * *